(12) United States Patent
Grinter et al.

(10) Patent No.: US 6,703,512 B1
(45) Date of Patent: Mar. 9, 2004

(54) INTERMEDIATES FOR THE PRODUCTION OF QUINOLONE CARBOXYLIC ACID DERIVATIVES

(75) Inventors: Trevor Grinter, Tonbridge (GB); Simon Howie, Tonbridge (GB)

(73) Assignee: SB Pharmco Puerto Rico Inc. of the United States Corporation Company, Hato Rey, PR (US)

(*) Notice: Subject to any disclaimer, the term of this patent is extended or adjusted under 35 U.S.C. 154(b) by 0 days.

(21) Appl. No.: 10/088,149
(22) PCT Filed: Sep. 1, 2000
(86) PCT No.: PCT/GB00/03358
§ 371 (c)(1), (2), (4) Date: May 30, 2002
(87) PCT Pub. No.: WO01/17961
PCT Pub. Date: Mar. 15, 2001

(30) Foreign Application Priority Data

Sep. 3, 1999 (GB) .............................................. 9920919

(51) Int. Cl.[7] .......................................... C07D 207/14
(52) U.S. Cl. ....................................................... 548/557
(58) Field of Search ......................................... 548/557

(56) References Cited

U.S. PATENT DOCUMENTS

| 5,633,262 A | 5/1997 | Hong et al. |
| 5,776,944 A | 7/1998 | Hong et al. |
| 5,869,670 A | 2/1999 | Hong et al. |
| 5,962,468 A | 10/1999 | Hong et al. |
| 6,307,059 B1 | 10/2001 | Chang et al. |

FOREIGN PATENT DOCUMENTS

| EP | 0 058 614 A1 | 8/1982 |
| EP | 0 183 129 A1 | 6/1986 |
| EP | 0 266 576 | 5/1988 |
| EP | 0 183 129 B1 | 8/1989 |
| EP | 0 326 891 | 8/1989 |
| EP | 0 541 086 A1 | 5/1993 |
| EP | 0 688 772 A | 12/1995 |
| EP | 0 688 772 A1 | 12/1995 |
| EP | 0 805 156 A1 | 5/1997 |
| EP | 0 688 772 B1 | 5/1999 |
| JP | 01 100165 A | 4/1989 |
| JP | 03 056479 A | 3/1991 |
| JP | 06-73056 A1 | 3/1994 |
| WO | WO 91/02526 A1 | 3/1991 |
| WO | WO 92/10191 A1 | 6/1992 |
| WO | WO 96/39406 A1 | 12/1996 |
| WO | WO 97/07098 A1 | 2/1997 |
| WO | WO 97/36874 A1 | 10/1997 |
| WO | WO 98 42705 A | 10/1998 |
| WO | WO 98/42705 A1 | 10/1998 |
| WO | WO 99/44991 A1 | 9/1999 |
| WO | WO 99/61420 A1 | 12/1999 |
| WO | WO 00/17199 A1 | 3/2000 |
| WO | WO 01/00209 A1 | 1/2001 |
| WO | WO 01/15695 A1 | 3/2001 |
| WO | WO 01/17961 A2 | 3/2001 |
| WO | WO 01/18002 A1 | 3/2001 |
| WO | WO 01/21176 A1 | 3/2001 |
| WO | WO 01/68649 A1 | 9/2001 |
| WO | WO 02/18336 A1 | 3/2002 |

OTHER PUBLICATIONS

M–J. Ahn, et al., "Effect of a New Fluoroquinolone LB20304a on Microflora of Caecum in Mice", *Yakhak Hoeji (Yakhak Hoechi)* Vol 40, No. 3, pp. 343–346 (1996).

M–J. Ahn, et al, "Post–Antibiotic Effect of LB20304, A New Quinolone Antibiotic", *Yakhak Hoeji (Yakhak Hoechi)* vol. 40, No. 3, pp. 347–350 (1996).

M–J. Ahn, et al., "InVivo Efficacy of LB20304a against Experimental Respiratory Tract Infection in Mice", *Yakhak Hoeji (Yakhak Hoechi)* vol. 40, No. 4, pp. 438–441 (1996).

CS Cooper et al, J. Med Chem, 35, 1992, 1392–1398.

G. Cormican, "Comparative Antimicrobial and Spectrum Activity of LB20304a, a New Fluoronated Naphthyridone Compound", *Abstracts of the 36th ICAAC*, 109 Abst F53 (1996).

MG Cormican et al, "Antimicrobial Activity and Spectrum of LB20304, a novel Fluoronaphthyridone", *Antimicrobial Agents and Chemotherapy*, Jan. 1997, 41, 204–211.

JM Domagala et al, J. Med. Chem., 31, 1988, 991–1001.

JM Domagala et al., J. Med. Chem., 34, 1991, 1142–1154.

C. Yong Hong, et al., "Novel Fluoroquinolone Antibacterial Agents Containing Oxime–Substituted (Aminomethyl) pyrrolidines: Synthesis and Antibacterial Activity of 7–(4–(Aminomethyl)–3–(methoxyimino) pyrrolidin–1–yl)–1–cyclopropyl–6–fluoro–4–oxo–1,4–dihydro [1,8] naphthyridine–3–carboxylic Acid (LB20304)", *J. Med. Chem.*, 40(22), pp. 3584–3593 (1997).

M–Y Kim et al., "In vitro activities of LB20304, a new Fluoroquinolone", *Arch. Pharm. Res.*, 1996, 19(1), 52–59.

J–H. Kwak, "Antimicrobial Activities of LB20304a, a New Quinolone Antibiotic", *The Journal of Applied Pharmacology* (4) pp. 378–384 (1996).

F. Marco, et al., "Äntimicrobial Activity of LB20304, a Fluoronaphthyridone, Tested Against Anaerobic Bacteria, *J. Antimicrobial Chemother* vol. 40, No. 4, pp. 605–607 (1997).

J–I Oh et al, "In vitro and in vivo evaluations of LB20304, a new Fluoroquinolone", *Antimicrobial Agents and Chemotherapy*, Jun. 1996, 40(6), 1564–1568.

K.–S. Paek et al., "Factors effecting in vitro activity of LB20304, a new fluoroquinolone", *Arch. Pharm. Res.*, 1996, 19(2), 143–147.

(List continued on next page.)

*Primary Examiner*—Patricia L. Morris
(74) *Attorney, Agent, or Firm*—Finnegan, Henderson, Farabow, Garrett, & Dunner, L.L.P.

(57) ABSTRACT

Chemical intermediates which are of use in the production of quinolone carboxylic acid derivatives having antibacterial activity.

16 Claims, No Drawings

OTHER PUBLICATIONS

K.-S. Paek et al., "Bactericidal activities of LB20304, a new Fluoroquinolone", *Arch. Pharm. Res.*, 1996, 19(4), 317–320.

M–K. Seo, "Pharmacokinetics of LB20304, a New Fluoroquinolone, in Rats and Dogs", *Arch. Pharm. Res.*, vol. 19, No. 5, pp. 359–367 (1996).

M–K. Seo et al., "High Performance Liquid Chromatographic Assay of a New Fluoroquinolone, LB20304, in the Plasma of Rats and Dogs", *Arch. Pharm. Res.* vol. 19, No. 6, pp. 554–558 (1996).

Patent Abstracts of Japan, Vol 015, No. 202 (C–0834), May 23, 1991 (JP03056479A, Mar. 12, 1991).

SB–265805, A Potent New Quinolone, 38th Annual Interscience Conference on Antimicrobial Agents and Chemotherapy, ICAAC, San Diego Convention Centre, 105–F Poster Session, New Fluoroquinolones II, Sep. 26th, 1998: cover page, contents page and Abstract Nos. F–087 through F–106.

INTERMEDIATES FOR THE PRODUCTION OF QUINOLONE CARBOXYLIC ACID DERIVATIVES

The present invention relates to novel compounds which are of use in the production of pharmaceutically active compounds, for example, quinolone carboxylic acid derivatives having antibacterial activity.

EP 688772 discloses novel naphthyridine carboxylic acid derivatives having antibacterial activity, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of the formula:

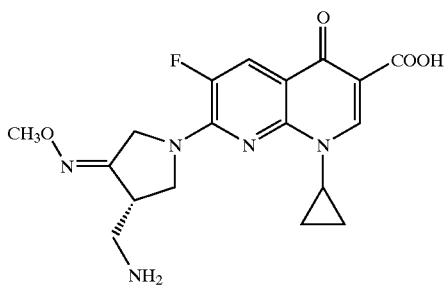

WO 98/42705 discloses (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

PCT/KR99/00099 (published after the priority date of the present application) discloses a process for the production of 4-aminomethyl-3-alkoxyiminopyrrolidines and salts thereof from aminomethylpyrrolidin-3-one and the corresponding alkoxylamine. Suitable salts of the 4-aminomethyl-3-alkoxyiminopyrrolidines are described as the hydrochloride, trifluoroacetate and sulfate salts.

The present invention relates to novel 4-aminomethyl-3-alkoxyiminopyrrolidine salts which are of use in the synthesis of pharmaceutically active compounds.

According to the invention there is provided a compound of formula (I):

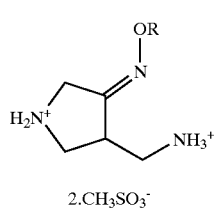

wherein R is $C_{1-4}$ alkyl or $C_{1-4}$ haloalkyl.

The compound of formula (I) is preferably 4-aminomethyl-3-methoxyiminopyrrolidinium dimethanesulfonate.

According to a further aspect of the invention there is provided a process for the production of a compound of formula (I) which comprises reaction of a compound of formula (II):

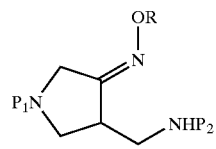

wherein R is as defined for formula (I) and $P_1$ and $P_2$, which may be the same or different, are amino protecting groups, with methanesulfonic acid.

Suitable protecting groups $P_1$ and $P_2$ include any suitable amino protecting groups which are removable by treatment with methanesulfonic acid. The preferred protecting group for both $P_1$ and $P_2$ is t-butoxycarbonyl.

The reaction of the compound of formula (II) and methanesulfonic acid is suitably carried out at a temperature between about 10° C. and about 50° C., more preferably at a temperature of 40–45° C.

The amount of methanesulfonic acid used to effect the deprotection of the compound of formula (II) is suitably 2 to 4 equivalents. For example, 2.4 equivalents, suitably used at a temperature of between 35° C. and 40° C.; or 3 equivalents, suitably used at ambient temperature. More preferably 2.5 equivalents used at a temperature of 40–45° C.

The reaction is suitably carried out in a solvent, for example, an alcohol such as methanol, ethanol, isopropanol, or n-propanol, dichloromethane, acetonitrile, acetone, methyl iso-butyl ketone, DME, THF, tert-butylmethyl ether, dioxane or ethyl acetate or a mixture of any of these. The solvent is preferably methanol. Suitably, up to 10 equivalents by volume of solvent may be used, e.g. about 4 equivalents.

The compounds of formula (II) may be prepared by the processes described in U.S. Pat. No. 5,633,262, EP 688772 and PCT/KR99/00099.

The compounds of formula (I) are useful as an intermediates for preparing quinolone antibacterials particularly those described in U.S. Pat. No. 5,633,262 and EP 688772. Thus according to a further aspect of the invention there is provided a process for the production of a compound of formula (III), or a pharmaceutically acceptable salt and/or hydrate thereof:

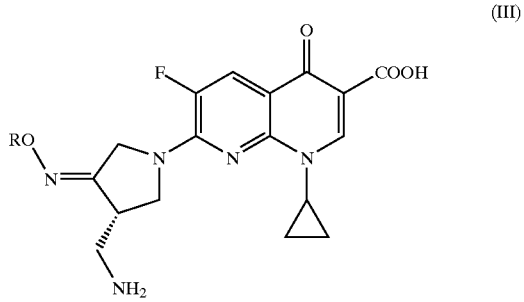

wherein R is as defined for formula (I), which comprises reaction of a compound of formula (I), with a compound of formula (IV):

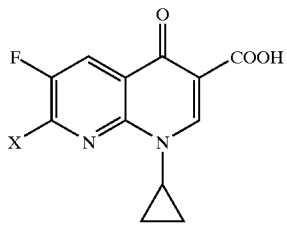

(IV)

wherein X is a leaving group, e.g. a halogen atom, preferably chlorine; and optionally forming a pharmaceutically acceptable salt and/or hydrate thereof.

Other suitable leaving groups X will be apparent to those skilled in the art.

The reaction of the compounds of formulae (I) and (IV) is preferably conducted in the presence of a base e.g. triethylamine. The reaction of the compounds of formulae (I) and (IV) is preferably conducted in a solvent, e.g. acetonitrile, an aqueous solvent such as aqueous acetonitrile or an aqueous alcohol and more preferably water. When water is used as solvent for this process the resulting compound of formula (III) is of superior quality to that obtained using other solvents. This leads to an improvement in the quality of the resulting drug substance as well as a process that may offer environmental advantages. Further details regarding the reaction of the compounds of formula (I) and (IV) can be found in U.S. Pat. No. 5,633,262 and EP 688772. The compounds of formula (IV) may be synthesised as described in U.S. Pat. No. 5,633,262 and EP 688772.

The compound of formula (III) produced according to this aspect of the invention is preferably (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof, preferably the sesquihydrate, as disclosed in WO 98/42705. The methanesulfonate and hydrates thereof may be synthesised from the free acid as described in WO 98/42705 and WO 00/17199.

The compounds of the invention have the advantage that they are stable, i.e. not hygroscopic. They can be isolated from the reaction in higher yield and purity than the corresponding dihydrochloride or free base. The dimesylate salts can be recrystallised if necessary, whereas the corresponding dihydrochloride or free base has not been successfully recrystallised. The dimesylate salts can be used to produce quinolone antibacterials of high purity and several advantages result from using this intermediate. For example, when the resulting drug substance is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof, it has improved colour and significantly lower levels of high molecular weight impurites compared to the drug substance produced using the corresponding dihydrochloride or free base as intermediate.

All publications, including but not limited to patents and patent applications, cited in this specification are herein incorporated by reference as if each individual publication were specifically and individually indicated to be incorporated by reference herein as though fully set forth.

The invention is illustrated by the following examples. However, it should be understood that the examples are intended to illustrate but not in any manner limit the scope of the invention.

EXAMPLE 1

Synthesis of 4-Aminomethyl-3-methoxyiminopyrrolidinium Dimethanesulfonate

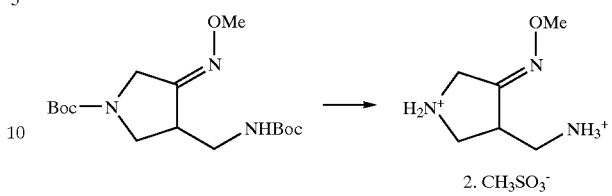

A solution of 1-(N-t-butoxycarbonyl)-4-(t-butoxycarbonylaminomethyl) pyrrolidin-3-methoxime (100 g) in methanol (660 mL) at 15–20° C. under nitrogen was treated with methanesulfonic acid (56.4 mL) over 5 min keeping the temperature below 30° C. The solution was stirred at 20–25° C. for 16–20 hrs. During this time the product precipitated forming a thick suspension. The product was isolated by filtration, washed with methanol (165 ml) and dried under vacuo at 25° C. to give the title compound 84 g (86%).

m.p. 189–193° C.; m/z: 144 (M+H)$^+$; $^1$H NMR (400 MHz, d$_6$-DMSO) δ: 9.27, (2H, brs), 7.95 (3H, brs), 4.01 (1H, d), 3.92 (1H, d), 3.87 (3H, s), 3.69 (1H, m), 3.26 (2H, m), 3.26 (2H, m), 3.15 (1H, m), 3.08 (1H, m), 2.39 (6H, s); Analysis: C, 28.64%, H, 6.25%, N, 12.46%; C$_8$H$_{21}$N$_3$O$_7$S$_2$ requires C, 28.65%, H, 6.31%, N, 12.53%.

EXAMPLE 2

Synthesis of 4-Aminomethyl-3-methoxyiminopyrrolidinium Dimethanesulfonate

A solution of 1-(N-t-butoxycarbonyl)-4-(t-butoxycarbonylaminomethyl) pyrrolidin-3-methoxime (100 g) in methanol (400 mL) at 20° C. under nitrogen was treated with methanesulfonic acid (47 mL, 70 g, 2.5 equiv) over 15 min keeping the temperature below 25° C. The solution was heated to 40–45° C. over 30 mins and maintained at this temperature for 4–5 hrs. During this time the product precipitated forming a thick suspension. The crude product was isolated by filtration under nitrogen and washed with methanol (200 mL). The crude product was suspended in methanol (4 volumes, approx. 360 mL) and heated to reflux for 1 hr. After cooling to 20° C. the suspension was stirred for 1 hour. The product was filtered, washed with methanol (2 volumes, approx. 180 ml) and dried under vacuum at 40° C. to give the title compound 73.8 g (78%). Characterising data were consistent with a standard sample of the title compound.

EXAMPLE 3

Synthesis of (R,S)-7-(3-Aminomethyl-4-syn-methoxyimino-pyrrolidin-1-yl)-1-cyclopropyl-6-fluoro-4-oxo-1,4-dihydro-1,8-naphthyridine-3-carboxylic Acid Triethylamine (5.1 ml) was added to 7-chloro-1-cyclopropyl-6-fluoro-4-oxo-1,4-dihydro-1,8-naphthyridine-3-carboxylic acid (3.05 g) in water (25 ml) at 15–20° C. and the mixture stirred for 20 min. 4-Aminomethyl-3-methoxyimino-pyrrolidinium dimethanesulfonate (3.86 g) was added, followed by water (5 ml), and the mixture stirred at 20–25° C. for 17¾ hours. The resulting product was filtered and the cake washed with water (30 ml) followed by ethanol (30 ml) and dried under vacuum at 50° C. to give the title compound as a white solid (4.23 g). (102% as is, 86% on assay). Characterising data were consistent with a standard sample of the title compound.

EXAMPLE 4

Synthesis of (R,S)-7-(3-Aminomethyl-4-syn-methoxyimino-pyrrolidin-1-yl)-1-cyclopropyl-6-fluoro-4-oxo-1,4-dihydro-1,8-naphthyridine-3-carboxylic Acid Methanesulfonate A solution of methanesulfonic acid (0.33 g, 3.43 mmol) in dichloromethane (1 ml) was added to a suspension of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (1.5 g at 89.9% purity, 3.46 mmol) in a mixture of dichloromethane (23.2 ml) and ethanol (2.7 ml) at 30° C. The mixture was stirred at 30° C. for 3 hours then cooled to 20° C. and filtered. The cake was washed with dichloromethane (20 ml) and dried at 50° C. under vacuum to give the title compound (1.71 g) (102% as is, 91% on assay). Characterising data were consistent with a standard sample of the title compound.

EXAMPLE 5

Synthesis of (R,S)-7-(3-Aminomethyl-4-syn-methoxyimino-pyrrolidin-1-yl)-1-cyclopropyl-6-fluoro-4-oxo-1,4-dihydro-1,8-naphthyridine-3-carboxylic Acid Methanesulfonate Sesquihydrate (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate (27.5 g at 91% purity, 51.4 mmol) was stirred in a mixture of isopropanol (150 ml) and water (75 ml) and heated until a clear solution was obtained (52° C.). The solution was cooled to 34° C. and seed crystals of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate added. The resulting suspension was allowed to cool to 25° C. over 1 hour and stirred for 18 hours. The slurry was cooled to 0–4° C., stirred for 2 hours, then filtered and the cake washed with isopropanol (30 ml). The product was sucked dry for 2 hours and then further dried at 50° C. under vacuum. The dried product was exposed to the atmosphere to give the sesquihydrate, 22.9 g (92%). Characterising data were consistent with a standard sample of the title compound.

What is claimed is:

1. A compound of formula (I):

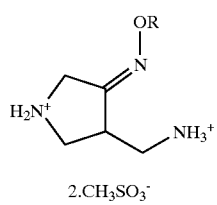

(I)

wherein R is $C_{1-4}$ alkyl or $C_{1-4}$ haloalkyl.

2. 4-aminomethyl-3-methoxyiminopyrrolidinium dimethanesulfonate.

3. A process for the production of a compound of formula (I) as defined in claim 1 which comprises reaction of a compound of formula (II):

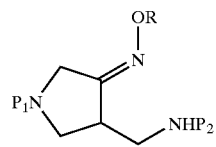

(II)

with methanesulfonic acid,
wherein R is as defined for formula (I); and $P_1$ and $P_2$, which may be the same or different, are amino protecting groups.

4. The process according to claim 3 wherein $P_1$ and $P_2$ are both t-butyloxycarbonyl.

5. The process according to claim 3 wherein the amount of methanesulfonic acid used to effect the deprotection of the compound of formula (II) is 2 to 4 equivalents.

6. The process according to claim 3 wherein the reaction is carried out at a temperature between about 10° C. and about 50° C.

7. The process according to claim 3 wherein the reaction is carried out in a solvent being methanol, ethanol, isopropanol, n-propanol, dichloromethane, acetonitrile, acetone, methyl iso-butyl ketone, DME, THF, tert-butylmethyl ether, dioxane, ethyl acetate, or a mixture of any of these.

8. The process according to claim 3 wherein the reaction is carried out in a solvent being methanol.

9. The process according to claim 3 wherein the reaction is carried out in a solvent, and wherein from about 4 equivalents to 10 equivalents by volume of the solvent are used.

10. A process for the production of the compound of claim 2 which comprises reaction of a compound of formula (II):

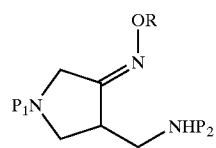

(II)

with methanesulfonic acid,
wherein R is methyl; and $P_1$ and $P_2$, which may be the same or different, are amino protecting groups.

11. The process according to claim 10 wherein $P_1$ and $P_2$ are both t-butyloxycarbonyl.

12. The process according to claim 10 wherein the amount of methanesulfonic acid used to effect the deprotection of the compound of formula (II) is 2 to 4 equivalents.

13. The process according to claim 10 wherein the reaction is carried out at a temperature between about 10° C. and about 50° C.

14. The process according to claim 10 wherein the reaction is carried out in a solvent being methanol, ethanol, isopropanol, n-propanol, dichloromethane, acetonitrile, acetone, methyl iso-butyl ketone, DME, THF, tert-butylmethyl ether, dioxane, ethyl acetate, or a mixture of any of these.

15. The process according to claim 10 wherein the reaction is carried out in a solvent being methanol.

16. The process according to claim 10 wherein the reaction is carried out in a solvent, and wherein from about 4 equivalents to 10 equivalents by volume of the solvent are used.

* * * * *